(12) United States Patent
Capote et al.

(10) Patent No.: US 8,372,121 B2
(45) Date of Patent: Feb. 12, 2013

(54) ADJUSTABLE COUPLING SYSTEMS FOR SPINAL STABILIZATION MEMBERS

(75) Inventors: Marco Dagoberto Capote, Memphis, TN (US); Frank Bono, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 964 days.

(21) Appl. No.: 11/703,958

(22) Filed: Feb. 8, 2007

(65) Prior Publication Data

US 2008/0195100 A1    Aug. 14, 2008

(51) Int. Cl.
*A61B 17/70* (2006.01)
(52) U.S. Cl. .................................... 606/260; 606/246
(58) Field of Classification Search .................. 606/260, 606/53, 57, 58, 60, 246, 250–278, 282, 90, 606/105; 403/322.1, 322.2
See application file for complete search history.

(56) References Cited

U.S. PATENT DOCUMENTS

| | | | |
|---|---|---|---|
| 3,260,541 A * | 7/1966 | Sadler et al. | 403/325 |
| 4,361,141 A | 11/1982 | Tanner | |
| 4,453,449 A * | 6/1984 | Hollmann | 89/1.806 |
| 4,656,698 A * | 4/1987 | Arakawa | 24/136 A |
| 4,771,767 A | 9/1988 | Steffee | |
| 4,773,402 A | 9/1988 | Asher et al. | |
| 4,854,304 A | 8/1989 | Zielke | |
| 4,927,286 A * | 5/1990 | Hobluigie et al. | 403/322.2 |
| 5,027,630 A * | 7/1991 | Stillwagon et al. | 70/391 |
| 5,053,034 A | 10/1991 | Olerud | |
| 5,154,718 A | 10/1992 | Cozad et al. | |
| 5,217,461 A | 6/1993 | Asher et al. | |
| 5,330,472 A | 7/1994 | Metz-Stavenhagen | |
| 5,330,474 A | 7/1994 | Lin | |
| 5,336,223 A | 8/1994 | Rogers | |
| 5,403,314 A | 4/1995 | Currier | |
| 5,425,732 A | 6/1995 | Ulrich | |
| 5,486,174 A | 1/1996 | Fournet-Fayard et al. | |
| 5,487,744 A | 1/1996 | Howard | |
| 5,562,660 A | 10/1996 | Grob | |
| 5,575,790 A | 11/1996 | Chen et al. | |
| 5,593,408 A | 1/1997 | Gayet et al. | |
| 5,630,816 A | 5/1997 | Saurat | |
| 5,643,260 A | 7/1997 | Doherty | |
| 5,658,284 A | 8/1997 | Sebastian et al. | |
| 5,993,449 A | 11/1999 | Schlapfer et al. | |
| 6,099,528 A | 8/2000 | Saurat | |
| 6,102,912 A | 8/2000 | Cazin et al. | |
| 6,106,527 A | 8/2000 | Wu et al. | |
| 6,171,311 B1 | 1/2001 | Richelsoph | |
| 6,176,860 B1 * | 1/2001 | Howard | 606/54 |
| 6,221,072 B1 * | 4/2001 | Termaten | 606/54 |
| 6,241,730 B1 | 6/2001 | Alby | |
| 6,328,739 B1 | 12/2001 | Liu et al. | |
| 6,328,741 B1 | 12/2001 | Richelsoph | |
| 6,379,072 B1 * | 4/2002 | Brown et al. | 403/31 |

(Continued)

FOREIGN PATENT DOCUMENTS

EP    0 584 803 A1    3/1994
WO    9732527 A    9/1997

*Primary Examiner* — Eduardo C Robert
*Assistant Examiner* — Jerry Cumberledge

(57) ABSTRACT

A spinal stabilization system includes a first stabilization member and a second stabilization member engaged to one another in end-to-end fashion. A coupling system adjustably secures the stabilization members in axial position relative to one another while allowing the relative axial positioning to be adjusted to accommodate growth or other condition or arrangement.

25 Claims, 9 Drawing Sheets

U.S. PATENT DOCUMENTS

| | | |
|---|---|---|
| 6,390,722 B1 * | 5/2002 | Godfrey et al. ............ 403/322.2 |
| 6,520,962 B1 | 2/2003 | Taylor et al. |
| 6,568,717 B1 * | 5/2003 | Le Clinche ................... 285/315 |
| 6,669,397 B1 * | 12/2003 | Christion ................... 403/322.2 |
| 6,676,661 B1 | 1/2004 | Benlloch et al. |
| 6,685,705 B1 | 2/2004 | Taylor |
| 7,175,622 B2 * | 2/2007 | Farris ........................... 606/250 |
| 7,195,632 B2 * | 3/2007 | Biedermann et al. ......... 606/250 |
| 7,935,134 B2 * | 5/2011 | Reglos et al. ................. 606/257 |
| 2001/0009632 A1 * | 7/2001 | Cross ........................ 403/322.2 |
| 2002/0197105 A1 * | 12/2002 | Chiang ..................... 403/322.2 |
| 2003/0233100 A1 * | 12/2003 | Santarella et al. .............. 606/99 |
| 2004/0220575 A1 | 11/2004 | Biedermann et al. |
| 2005/0154388 A1 | 7/2005 | Roussouly et al. |
| 2005/0171537 A1 | 8/2005 | Mazel et al. |
| 2005/0177164 A1 * | 8/2005 | Walters et al. .................. 606/72 |
| 2005/0177166 A1 * | 8/2005 | Timm et al. .................... 606/73 |
| 2005/0228376 A1 | 10/2005 | Boomer et al. |
| 2005/0228378 A1 | 10/2005 | Kalfas et al. |
| 2005/0234456 A1 | 10/2005 | Malandain |
| 2005/0277925 A1 | 12/2005 | Farris |
| 2005/0277932 A1 | 12/2005 | Farris |
| 2006/0241622 A1 | 10/2006 | Zergiebel |
| 2007/0100341 A1 * | 5/2007 | Reglos et al. ................... 606/61 |
| 2007/0270964 A1 | 11/2007 | Strohkirch, Jr. et al. |
| 2009/0306717 A1 * | 12/2009 | Kercher et al. ............... 606/258 |

* cited by examiner

ADJUSTABLE COUPLING SYSTEMS FOR SPINAL STABILIZATION MEMBERS

BACKGROUND

The spine is subject to various pathologies that compromise its load bearing and support capabilities. Such pathologies of the spine include, for example, degenerative diseases, the effects of tumors and, of course, fractures and dislocations attributable to physical trauma. In the treatment of diseases, malformations or injuries affecting spinal motion segments (which include two or more adjacent vertebrae and the disc tissue or disc space therebetween), and especially those affecting disc tissue, it has long been known to remove some or all of a degenerated, ruptured or otherwise failing disc. It is also known that artificial discs, fusion implants, or other interbody devices can be placed into the disc space after disc material removal. External stabilization of spinal segments alone or in combination with interbody devices also provides advantages. Elongated rigid plates, rods and other external stabilization devices have been helpful in the stabilization and fixation of a spinal motion segment, in correcting abnormal curvatures and alignments of the spinal column, and for treatment of other conditions.

While external stabilization systems have been employed along the vertebrae, the geometric and dimensional features of these systems and patient anatomy constrain the surgeon during surgery and prevent optimal placement and attachment along the spinal column. For example, elongated, one-piece spinal rods can be difficult to maneuver into position along the spinal column, and also provide the surgeon with only limited options in sizing and selection of the rod system to be placed during surgery. Furthermore, there remains a need to provide spinal stabilization systems which correct one or more targeted spinal deformities while also preserving the ability to adjust the systems for optimal fit during the surgical procedure and in subsequent procedures.

SUMMARY

A spinal stabilization system includes a first stabilization member and a second stabilization member engaged to one another in end-to-end fashion. A coupling system adjustably secures the stabilization members in axial position relative to one another while allowing the relative axial positioning to be adjusted to accommodate growth or other condition or arrangement.

According to one aspect, a spinal stabilization system includes a first elongated stabilization member extending along a longitudinal axis between a first end and an opposite second end and a second elongated stabilization member extending along the longitudinal axis between a first end and an opposite second end so that the first end of the first stabilization member and the second end of the second stabilization member are positioned adjacent to one another. There is further provided a coupling system including a first member having a first end engaged to an end portion at the first end of the first stabilization member and a second end engaged to the second end of the second stabilization member. The coupling system further includes a lock coupled between the first member and the end portion of the first stabilization member that has a locked position that is configured to maintain a relative axial positioning of the first and second stabilization members. The lock is movable along the longitudinal axis to release the end portion of the first stabilization member from the first member to allow the relative axial positioning of the first and second stabilization members to be adjusted.

According to another aspect, a spinal stabilization system includes a first elongated stabilization member extending along a longitudinal axis between a first end and an opposite second end and a second elongated stabilization member extending along the longitudinal axis between a first end and an opposite second end so that the first end of the first stabilization member and the second end of the second stabilization member are positioned adjacent to one another. There is also a coupling system including a lock, a first member having a first end engaged to an end portion at the first end of the first stabilization member and a second end engaged to the second end of the second stabilization member. The end portion of the first stabilization member is engaged in a passage of the first member by the lock being axially biased to a locked position to maintain a relative axial positioning of the first and second stabilization members. The coupling system is operable to release the end portion from the locked position to allow the relative axial positioning of the first and second stabilization members to be adjusted.

According to yet another aspect, a method for spinal stabilization comprises: engaging a first elongate stabilization member to a first vertebra of a spinal column with a first anchor; engaging a second elongate stabilization member to a second vertebra of the spinal column with a second anchor; coupling the first stabilization member and the second stabilization member to a coupling system between the first and second anchors; locking the first and second stabilization members in position relative to one another at a first length between the first and second anchors in a first surgical procedure; accessing the coupling system in a second surgical procedure; and manipulating the coupling system to adjust the length of the first and second stabilization members between the first and second anchors.

According to another aspect, a method for assembling a spinal stabilization system comprises: providing a first elongate stabilization member with a first portion for attachment to the spinal column and a first end portion; providing a second elongate stabilization member with a second portion for attachment to the spinal column and a second end portion, wherein the first and second portions extend along a longitudinal axis; providing a coupling system including a first member and a locking member; connecting the second end portion to the first member; and locking the first end portion of the first stabilization member to the first member with a locking member biased along the longitudinal axis.

Related features, aspects, embodiments, objects and advantages will be apparent from the following description.

DESCRIPTION OF THE ILLUSTRATED EMBODIMENTS

Figure 1:
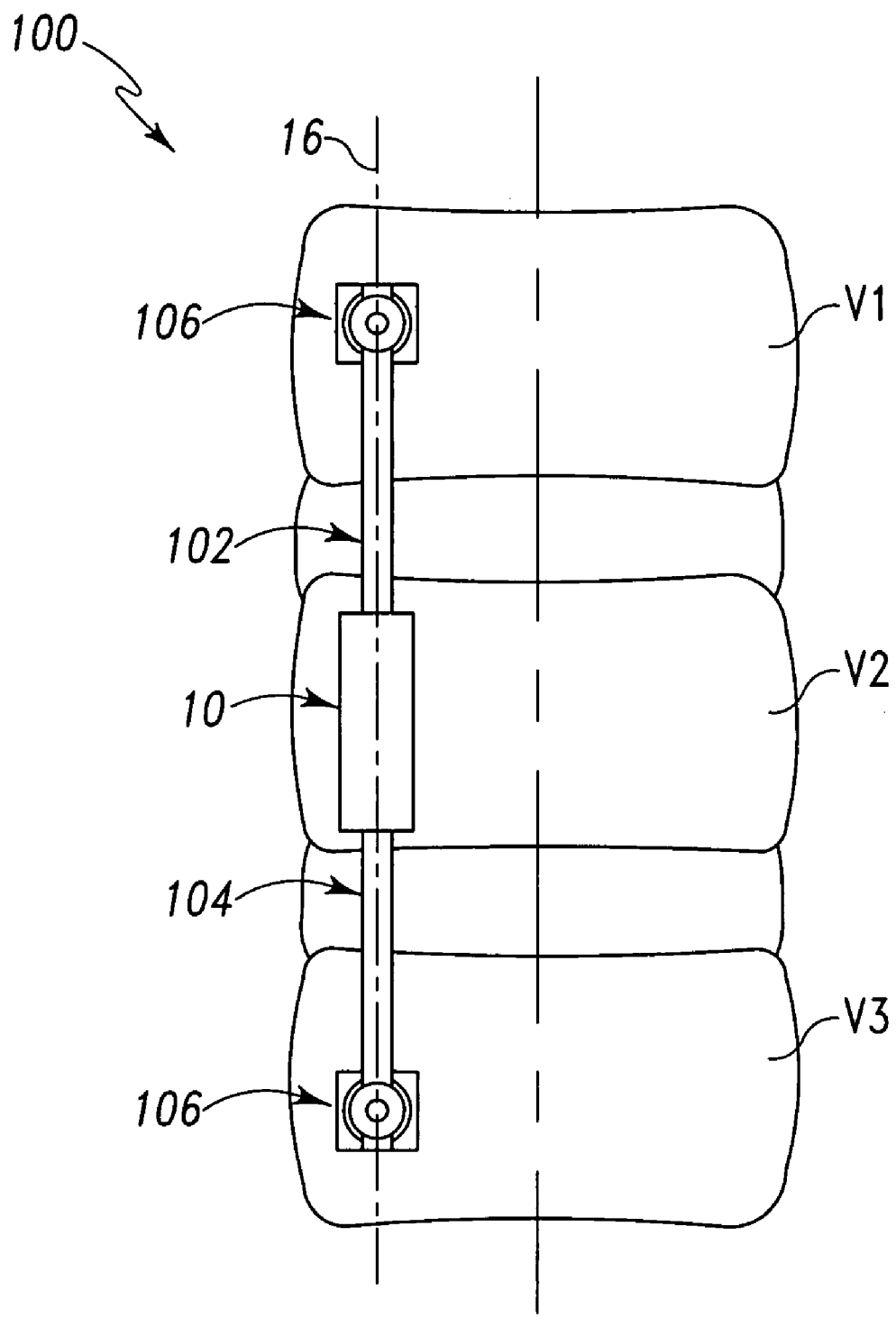
FIG. 1 is a diagrammatic elevation view of a posterior portion of the spinal column with a stabilization system shown diagrammatically in attachment with the spinal column.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

FIG. 1 illustrates posterior spinal stabilization system 100 located along a spinal column of a patient. More specifically, stabilization system 100 can be affixed to vertebrae V1, V2, V3 of the spinal column segment from a posterior approach. Applications along two vertebrae or four or more vertebrae are also contemplated. Implant system 100 generally includes one or more coupling systems 10 (shown diagrammatically in FIG. 1 and discussed further below) and elongated stabilization members 102, 104 extending in opposite directions from coupling system 10 that selectively interconnect with coupling system 10 and are anchored to bony structure along the spinal column. Stabilization members 102, 104 may be a spinal rod, plate, bar, or other elongated element having a length and configuration to extend outside the disc space between at least two vertebrae. Stabilization members 102, 104 may be solid or hollow along some or all of its length and/or may be of homogenous or heterogeneous composition. In stabilization system 100, anchors 106 (shown diagrammatically) are affixed to various locations of the spinal column segment and secure stabilization members 102, 104 to selected vertebrae, such as vertebrae V1, V3 as shown. In one embodiment, anchors 106 are engaged to the pedicles of the vertebrae. Spinal stabilization system 100 may be used for, but is not limited to, treatment of degenerative spondylolisthesis, fracture, dislocation, scoliosis, kyphosis, spinal tumor, and/or a failed previous fusion. Applications in other approaches and implantation locations along the spinal column are also contemplated, including anterior, antero-lateral, and lateral approaches and locations.

Illustrative embodiments disclosed herein are directed to coupling systems for adjustably securing spinal stabilization members to one another in end to end fashion in either axial alignment or in axially offset relationships. The stabilization members are engaged to respective ones of first and second vertebrae with an anchor, while the coupling system adjustably connects the stabilization members to one another between the anchors. The coupling system allows the length of the stabilization members between the anchors to be readily increased or decreased to accommodate, for example, growth of the patient.

In one embodiment the coupling systems include an intermediate locking member and an outer member that are concentrically disposed. A locking element is movably contained within an opening that extends through a sidewall of the intermediate locking member to releasably engage an inner member disposed within the intermediate locking member. The inner member can be an end of one of the stabilization members, or an end member engaged to an end of one of the stabilization members. The intermediate locking member is displaceable longitudinally in first and second directions relative to the outer member. Displacement of the intermediate locking member in the first direction tends to force the locking element into contact with both of the inner and outer members. A biasing member urges the intermediate locking member in the first direction. Displacement of the intermediate locking member in the second direction allows the locking element to be displaced out of contact with the inner member so that the inner member can be adjusted in axial positioning within the intermediate and outer members to increase or decrease the length of the first and second stabilization members between connection locations with the spinal column.

Figure 2:
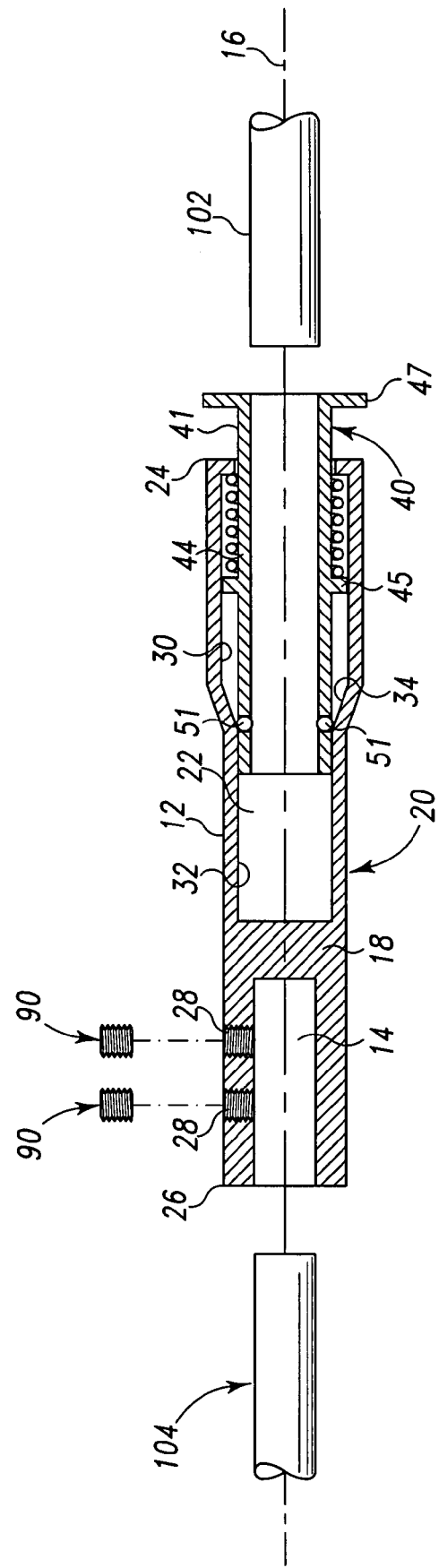
FIG. 2 is an exploded, longitudinal section view of one embodiment coupling system and a portion of the stabilization members.
Figure 3:
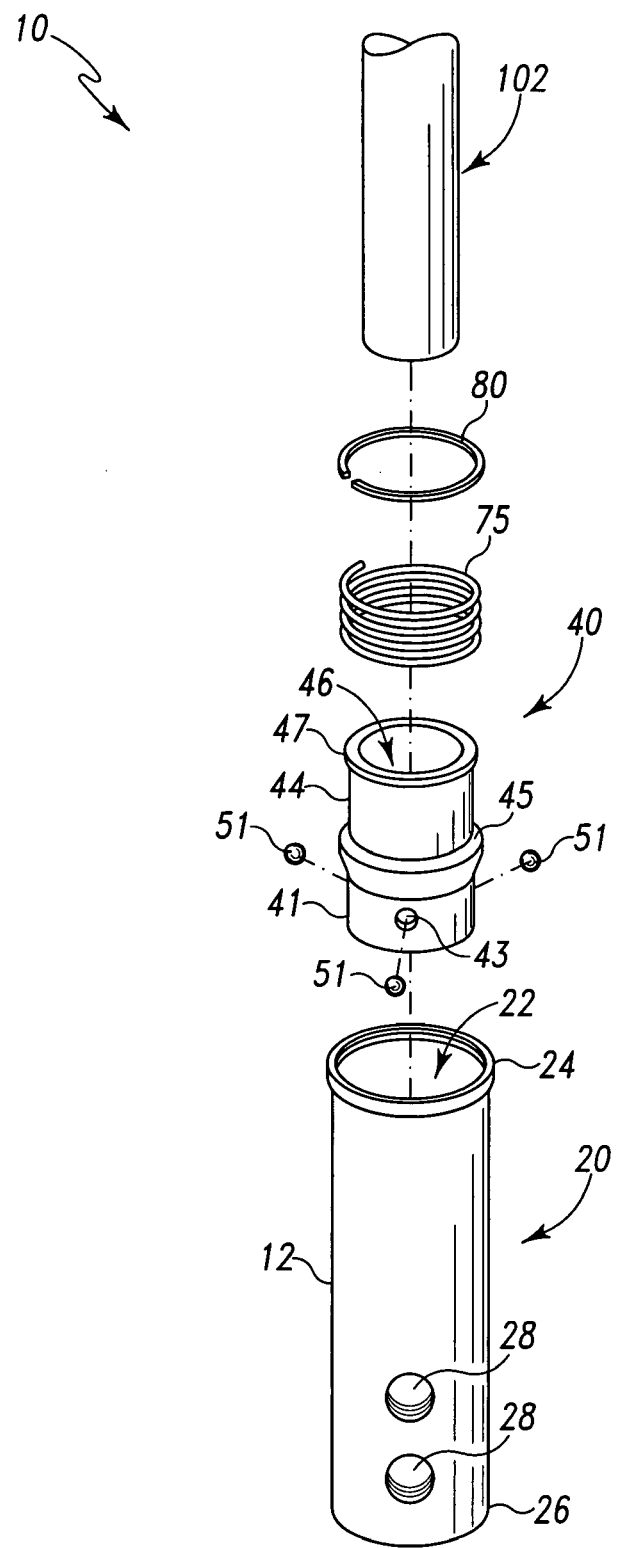
FIG. 3 is an exploded perspective view of the coupling system of FIG. 2.

FIGS. 2 and 3 illustrate one embodiment of a coupling system 10 for securing elongate spinal stabilization members 102, 104 in end-to-end fashion along the spinal column. Coupling system 10 includes a first member 20 that, in one embodiment, includes a hollow elongated first body 12 having an open first passage 22 that extends through at least a portion of its length. First passage 22 opens at least at first end 24. In the illustrated embodiment, body 12 includes a second passage 14 that opens at a second end 26 that is opposite first end 24 and longitudinally receives stabilization member 104 therein. A partition wall 18 is provided between passages 14, 22 to prevent stabilization member 104 from encroaching into first passage 22. Other embodiments contemplate that partition wall 18 is not provided, or is not solid as shown. Body 12 also includes bores 28 in communication with second passage 14. Engaging members 90 are engageable in respective ones of the bores 28 to contact stabilization member 104 and maintain it in engagement with first member 20 in second passage 14. Engaging members can be set screws, plugs or other suitable device for engaging the stabilization member to first member 20.

Coupling system 10 also includes a lock 40 that is configured to be axially received in first passage 22 and project axially from first end 24. Lock 40 includes a lock body 41 having one or more openings 43 in a lower section thereof. One embodiment of lock 40 includes one or more locking elements 51 that fit within openings 43. Lock 40 also includes a receiving passage 46 extending therethrough through which stabilization member 102 is axially received. Locking elements 51 may move within openings 43 between a locked position in engagement with stabilization member 102 to fix it in position in passage 46 and an unlocked position where stabilization member 102 is slidable in passage 46. FIG. 3 also shows a retainer 80 and biasing member 75 that cooperate to retain lock body 41 within first passage 22 of first member 20. As described below, biasing member 75 may also maintain locking elements 51 in the locked position.

Figure 4:
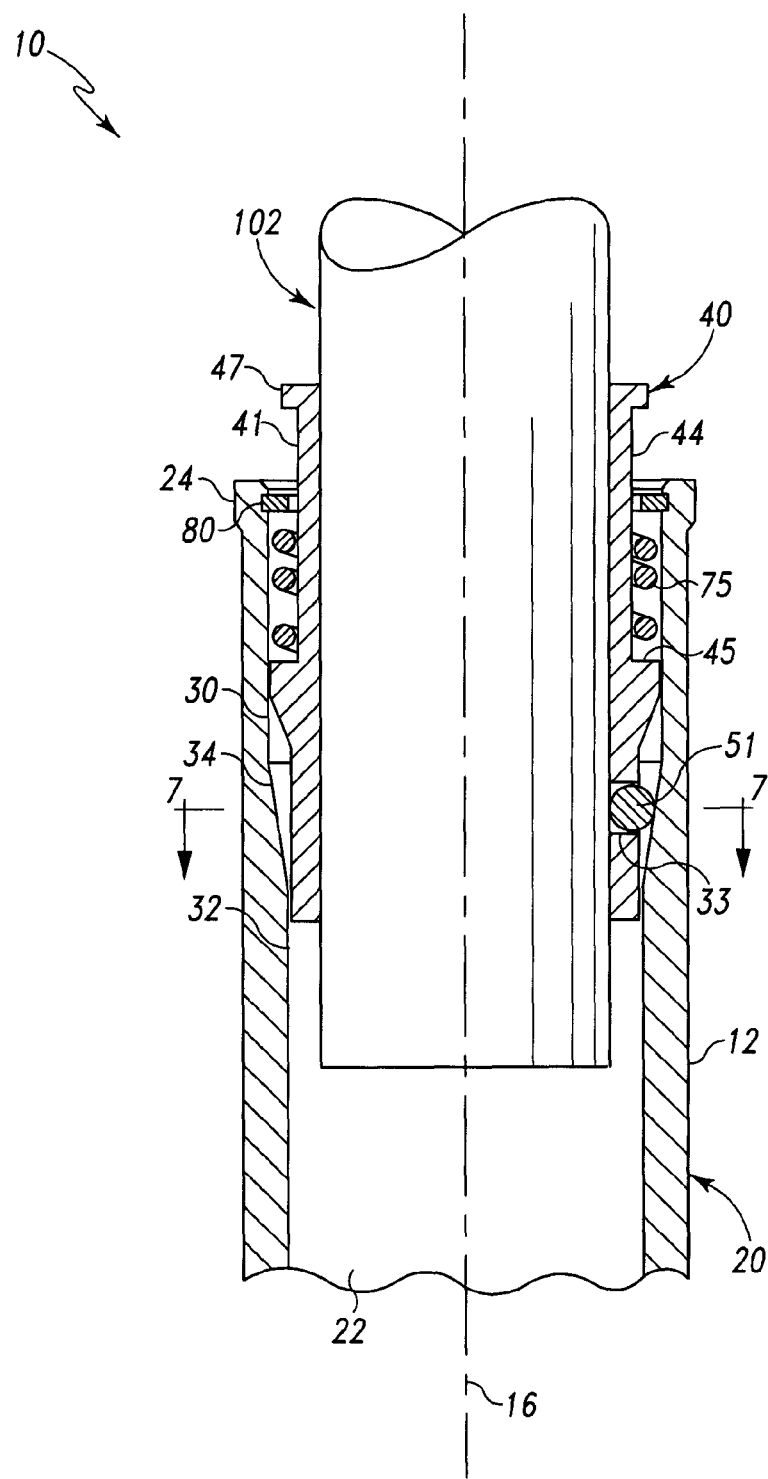
FIG. 4 is a longitudinal section view of the coupling system of FIG. 2 in a first position.

FIG. 4 illustrates a longitudinal cross section of a portion of coupling system 10. In one embodiment, first member 20 and lock 40 each include a substantially circular cross-sectional shape with first passage 22 also being substantially circular. In other embodiments, first member 20 and first passage 22 include non-circular cross-sectional shapes. Generally, for either configuration, first member 20, lock body 41, and stabilization member 102 are arranged concentrically. First passage 22 tapers from a first width at wall section 30 disposed towards the first end 24 to a second, narrower width at wall section 32 disposed towards the second end 26. A tapered wall section 34 is disposed therebetween and provides a gradual transition between the different widths.

In one embodiment, lock body 41 further includes an intermediate neck section 44 with a reduced width that is spaced inward from the inner side of wall section 30 of first member 20. A shelf 45 having a larger width extends around neck section 44 is positioned at an inner end of neck section 44 adjacent to the inner section including openings 43. A cap 47 extends radially outwardly from neck 44 at an outer end of the lock body 41 opposite its inner section. Cap 47 provides a location at which lock 40 is readily grasped and axially manipulated, as discussed further below.

Lock 40 further includes one or more locking elements 51 movably positioned at openings 43. In one embodiment, locking elements 51 comprise spherical balls, such as ball bearings. In another embodiment, locking elements 51 include other shapes. For example, in one embodiment described below, the locking element 51 includes a substantially cylindrical shape. In embodiments having plural locking elements 51, each of the locking elements 51 may include the same or different shapes and sizes. In one embodiment, each locking element 51 travels into and out of the respective opening 43 in which it is received. As illustrated in the embodiment of FIG. 4, a thickness of the locking element 51 is greater than a thickness of the inner section of lock body 41 forming opening 43, although other sections of the lock body 41 may include a greater thickness than that of locking element 51. Therefore, axial movement of lock body 41 into first passage 22 relative to first member 20 causes locking elements 51 to move radially inwardly when sliding along tapered wall section 34.

In FIG. 4, coupling system 10 is depicted with lock 40 in the first, locked position between an end portion of stabilization member 102 in receiving passage 46 and tapered wall section 34 along first passage 22. In the locked position, the overall length of stabilization members 102, 104 between anchors 106 is fixed in compression and in distraction. In another embodiment, the minimum length of stabilization members 102, 104 between anchors 106 is fixed while axial extension of the length is permitted in response to tension loading of the stabilization members 102, 104.

Figure 5:
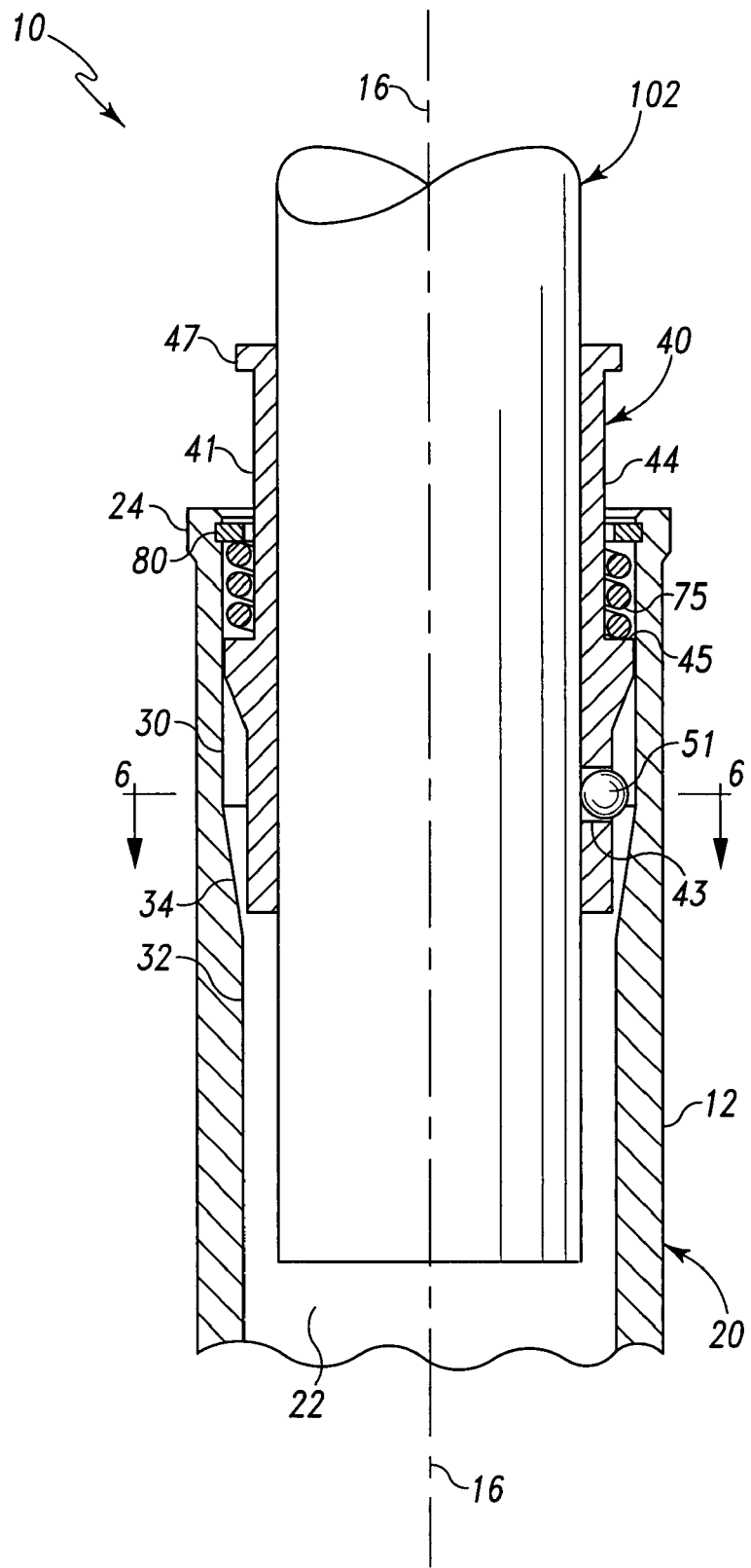
FIG. 5 is a longitudinal section view of the coupling system of FIG. 2 in a second position.

FIG. 5 illustrates coupling system 10 in a second, unlocked position. In this position, stabilization member 102 extends into passages 22, 46 of first member 20 and lock body 41, respectively. Lock body 41 is positioned within first member 20 with openings 43 aligned at wall section 30 where first passage 22 includes a wider first width. In one embodiment, a space formed between stabilization member 102 and the wall section 30 of first passage 22 is greater than the thickness of locking elements 51, allowing locking elements 51 to freely move in openings 43 and thus preventing binding or wedging of locking elements 51 with the end portion of stabilization member 102 and first member 20.

Figure 6:
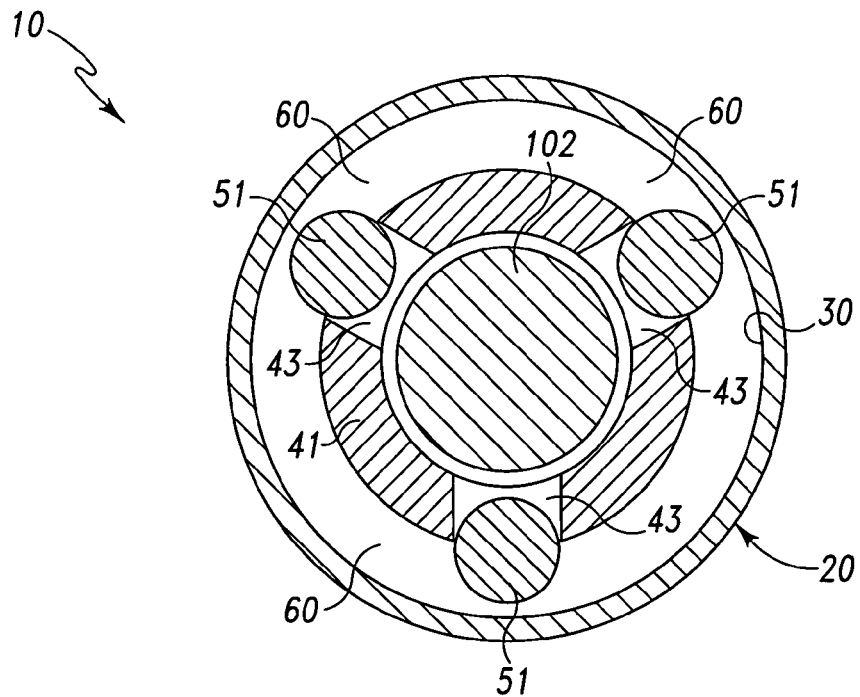
FIG. 6 is a cross-sectional view of the coupling system along line 6-6 of FIG. 5.

FIG. 6 is a cross-sectional view of the unlocked coupling system 10 of FIG. 5. In this position, space 60 formed between stabilization member 102 and the wall section 30 of first member 20 is greater than the thickness of locking elements 51. Thus, locking elements 51 may move within space 60 and stabilization member 102 may move axially relative to first member 20 and lock body 41 to either increase or decrease the overall length of stabilization members 102, 104 between anchors 106.

Figure 7:
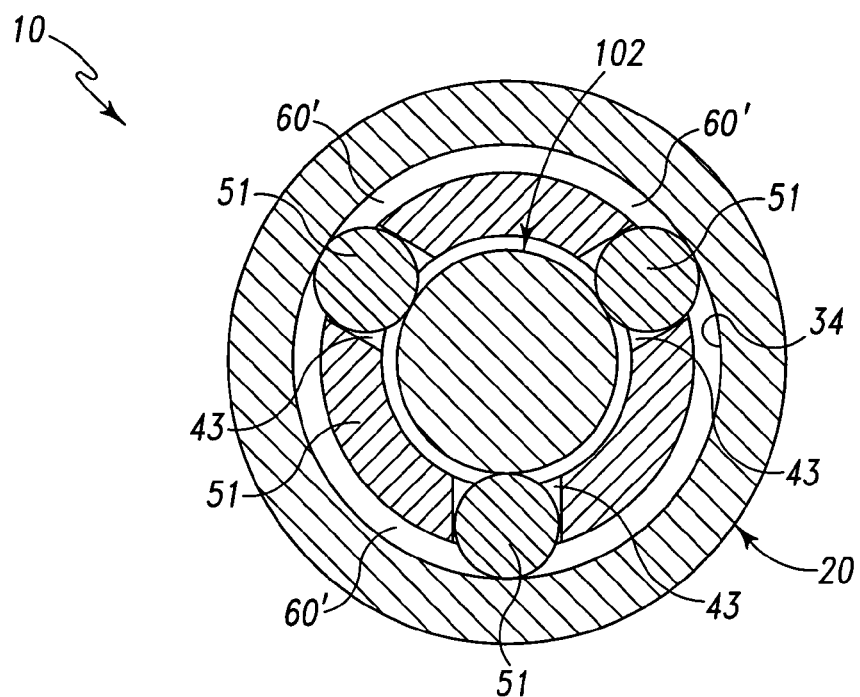
FIG. 7 is a cross-sectional view of the coupling system along line 7-7 of FIG. 4.

FIGS. 4 and 7 illustrate coupling system 10 in the locked position. In this configuration, lock body 41 is moved axially into first member 20. Openings 43 are now aligned at tapered wall section 34 where space 60' formed between stabilization member 102 and first member 20 is less than the thickness of locking elements 51. This causes locking elements 51 to move inwardly through the respective openings 43 and into contact with the end portion of stabilization member 102 to lock stabilization member 102 to first member 20 and maintain the overall length of stabilization members 102, 104 between anchors 106.

Due to the orientation of tapered wall section 34, stabilization member 102 may still extend relative to the first member 20 from the locked position even though axial compression or shortening of the length between anchors 106 is prevented. Tapered wall section 34 produces a decreasing width of first passage 22 in the direction in which stabilization members 102, 104 are moved axially toward one another. The decreasing width creates greater interference to provide a wedge effect and prevent further decreasing of the length of the stabilization system 100 between anchors 106. Therefore, locking elements 51 may apply a greater force on the stabilization member 102 the further stabilization member 102 and lock body 41 are inserted into first passage 22 of first member 20.

In one embodiment, a biasing mechanism 75 is positioned between first member 20 and lock 40. A first end of biasing mechanism 75 contacts shelf 45 of lock body 41. Retainer 80 is attached to the inner wall of body 12 adjacent first end 24 and forms a contact surface for a second end of biasing mechanism 75. In the illustrated embodiment, biasing mechanism 75 includes a cylindrical configuration that is disposed around neck 44 of lock body 41. In one specific embodiment, biasing mechanism 75 is a coil spring.

Biasing mechanism 75 applies a force on lock body 41 to normally bias or maintain lock body 41 towards the locked position. In one form, the force is sufficient to lock coupling system 10 so that stabilization member 102 is not movable further into first member 20 or movable out of first member 20 unless lock 40 is displaced to the unlocked position against the bias of biasing mechanism 75. Unlocking coupling system 10 is accomplished by moving lock body 41 away from first end 24 of first member 20 and against the biasing force applied by biasing mechanism 75. In one embodiment, grasping and pulling the cap 47 away from first end 24 and along stabilization member 102 will unlock lock 40 when locking members 51 are aligned with wall section 30 of first member 20.

Figure 8:
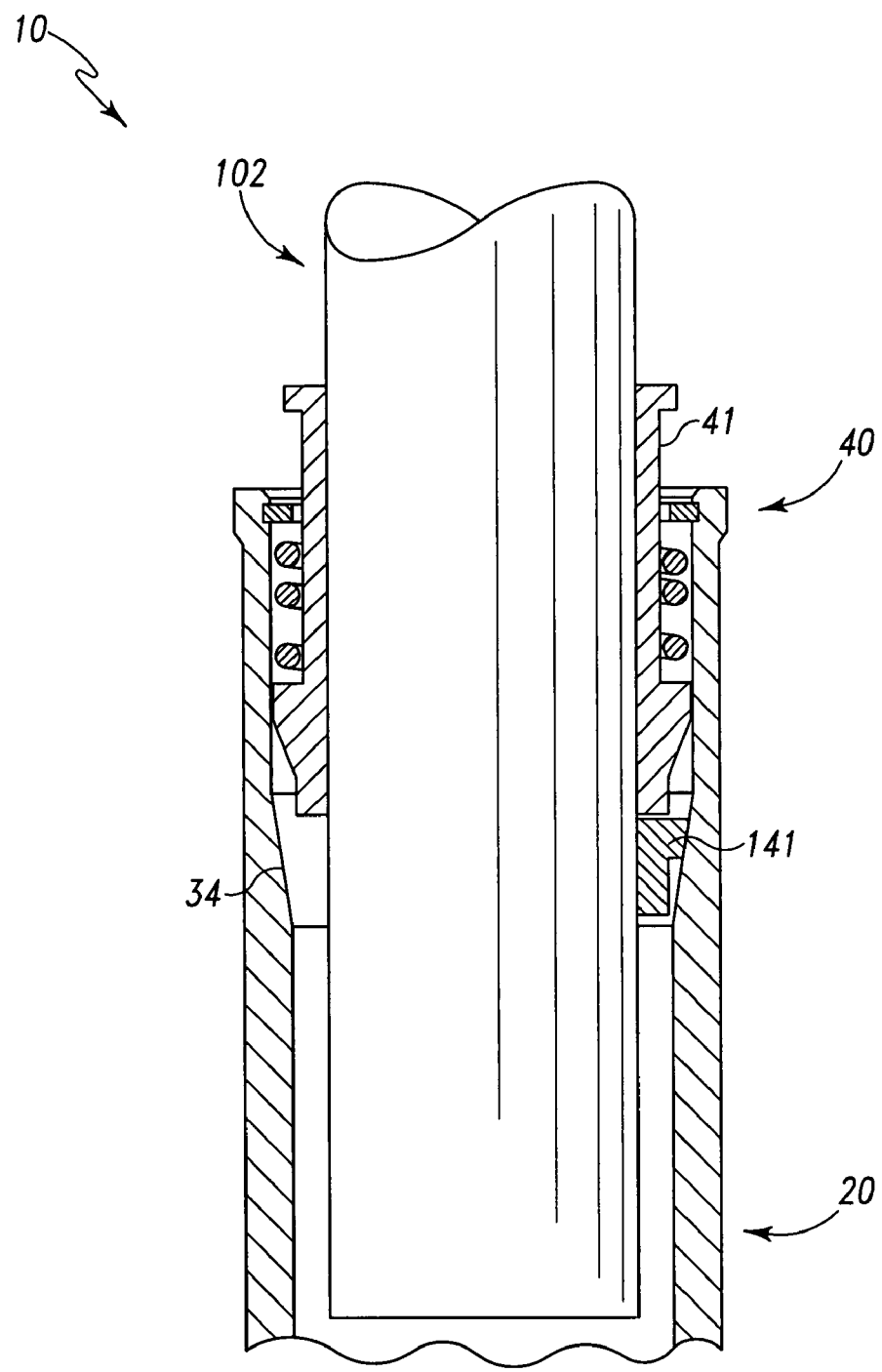
FIG. 8 is a longitudinal section view of another embodiment coupling system.
Figure 9:
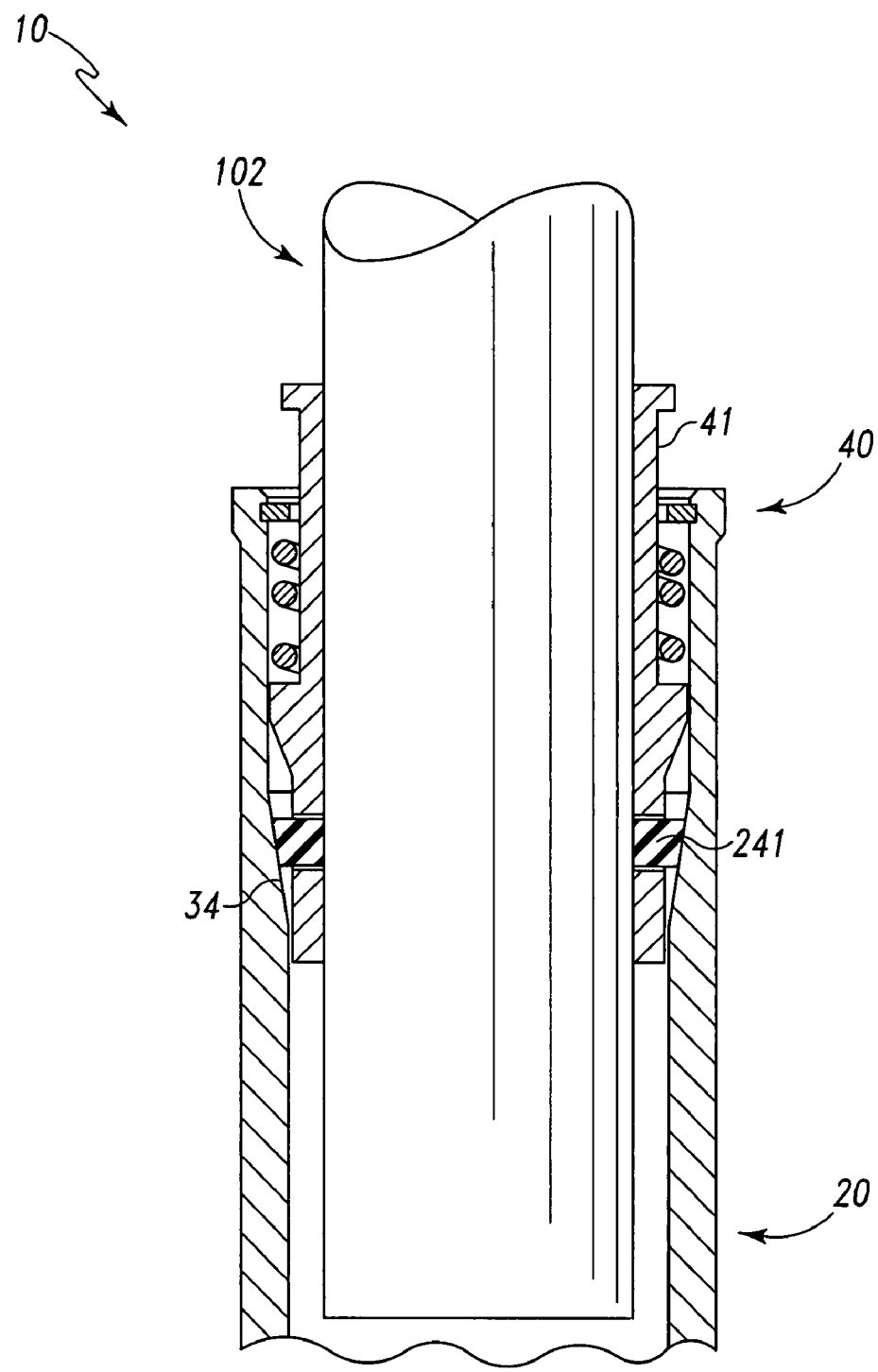
FIG. 9 is a longitudinal section view of another embodiment coupling system.

Locking elements 51 may further include a variety of shapes and sizes. Embodiments as illustrated in FIGS. 3-7 incorporate a locking element 51 including a spherical shape that moves within the openings 43. Another embodiment such as that illustrated in FIG. 8 incorporates a locking element 141 that includes a rectangular shape with an outer lip to contact the tapered wall section 34 in the locked position. Locking element 141 is located outside lock body 41' and is positioned in abutting engagement with the end thereof. In another embodiment shown in FIG. 9 a rectangular locking element 241 is provide with an outer tapered outer surface profile that engages tapered wall section 34 when in the locked position. Locking element 241 is positioned within an opening in the body of lock 40.

The number of locking elements 51 may vary depending upon the application. Certain embodiments feature multiple locking elements 51. For embodiments with multiple locking elements 51, the elements 51 may be positioned within the same plane relative to the lock body 41. In other embodiments, two or more of the locking elements 51 may be positioned within different planes about lock body 41. In one embodiment, a single locking element locks the coupling system 10. For example, locking elements 141 or 241 may be in the form of a ring extending around all or a substantial portion of the lock body. The locking element may be split to allow radial compression and expansion of the locking element or form a continuous ring to resist radial compression and expansion.

Figure 10:
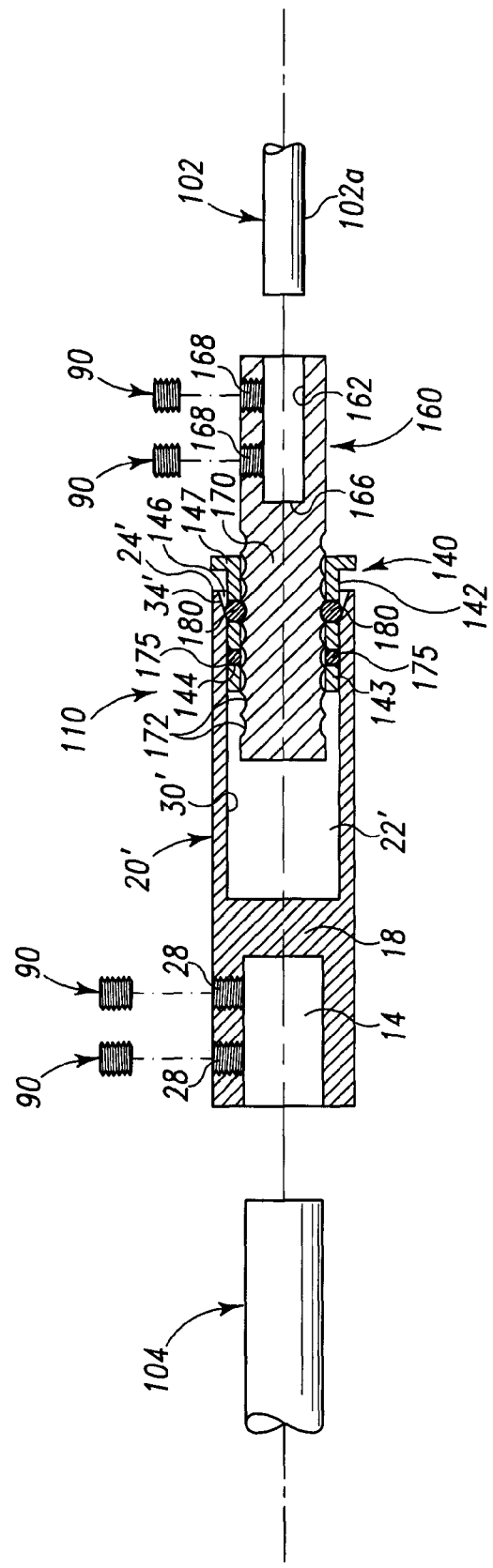
FIG. 10 is an exploded, longitudinal section view of another embodiment coupling system and a portion of the stabilization members.

FIG. 10 shows a longitudinal section view of another embodiment coupling system 110 to secure stabilization members relative to one another. Coupling system 110 includes a first member 20' that is similar to first member 20 discussed above. However, first member 20' includes a first passage 22' that has a wall section 30' of substantially uniform width along the entire length of first passage 22' that receives the lock body. First end 24' of first member 20' includes an inwardly tapered wall section 34' around the end opening into first passage 22'. While passage 22' can be cylindrical such as shown with respect to passage 22 discussed above, it is contemplated that passages 22, 22' can include any suitable shape, including square, rectangular, oval, and non-circular shapes.

First stabilization member 102 is shown with an end portion that is formed by a second member 160 removably coupled to an elongated portion 102a where portion 102a is positioned along and secured to the spinal column with anchor 106. Second member 160 has a receiving passage 162 opening at first end 164 of second member 160. Receiving passage 162 extends axially to a blind end 166, and is sized to receive portion 102a of stabilization member 102 therein. Engaging members 90 are secured in bores 168 to engage stabilization member 102 in receiving passage 162. Second member 160 also includes a second end portion 170 extending axially from end 166. Second end portion 170 is provided with a series of longitudinally spaced grooves or scallops 172 therealong. Second end portion 170 is sized and shaped to be received in passage 22' and includes a shape that is similar to the shape of passage 22'. End portion 170 can include a circular, square, rectangular, or non-circular cross-sectional shape. Non-circular shapes can limit or prevent rotation of the second member 160 relative to first member 20'.

Lock 140 is provided in first passage 22' between second end portion 170 and wall section 30'. Lock 140 includes a lock body 142 having a cylindrical shape with a central passage to receive second end portion 170 of second member 160 therethrough. Lock 140 also includes an outer cap or flange 147 extending about lock body 142 to facilitate grasping of it by hand. Lock body 142 includes inner wall openings 144 adjacent an inner end 143 of locking body 142, and outer openings 146 adjacent cap 147 of lock body 140. A biasing member 175 in the form of a spring wire or other device is engaged to first member 20' and extends into inner wall openings 144 to bias lock 140 into first member 20' while allowing lock body 142 to axially translate in first passage 22' along end portion 170 of second member 160.

Locking elements 180 are provided in outer openings 146 and in abutting engagement with tapered wall section 34' and second end portion 170 to axially secure second member 160, and thus stabilization member 102, in position relative to stabilization member 104. Second end portion 170 is provided with a series of groove or scallops 172 that receive locking elements 180 and further enhance the engagement of locking elements 180 with second end portion 170 to prevent relative movement between first member 20' and second member 160 in response to axial compression or tension loading of stabilization members 102, 104. To allow adjustment in the axial location of stabilization member 102 relative to stabilization member 104, locking elements 180 are displaced from scallops 172, allowing second end portion 170 to translate in lock body 142. Second end portion 170 is moved into or out of first receptacle 22' through lock body 142 to provide a desired overall length for stabilization members 102, 104, and then lock 140 is released for re-engagement of locking elements 180 with tapered wall section 34' and the scallops 172 along second end portion 170.

In another embodiment, it is contemplated that stabilization member 102 includes an end portion with second member 160 and is employed with coupling system 10 discussed above so that second end portion 170 is engaged by the locking members 51, 141, or 241. In another embodiment, the end portion of stabilization member 102 can be integral with the portion 102a extending along the spinal column, and the integral end portion could be configured like end portion 170 discussed above, or include any same or different configuration than portion 102a.

In use, coupling systems 10, 110 are employed to assemble stabilization members 102, 104 in a desired relative axial positioning so that the assembly can be secured to the spinal column to provide a spinal stabilization system. Each of the stabilization members 102, 104 are secured to respective vertebrae of the spinal column with anchors 106. The length of the stabilization members 102, 104 between anchors 106 is adjusted by adjusting the location of stabilization member 102 in the respective coupling system 10, 110 by manipulating lock 40, 140. In one procedure, a length for stabilization members between anchors 106 is selected so that the no net force is applied to anchors 106 by the stabilization members, and the respective coupling system 10, 110 is manipulated to lock the stabilization members at this selected length. Over time, the distance between anchors 106 may increase as a result of patient growth or other condition. In procedures where it is not desired to constrain such growth, coupling system 10, 110 can then be accessed in a second procedure to adjust the length of stabilization members 102, 104 between anchors 106 to provide the desired stabilization effect. Coupling systems 10, 110 can be accessed in a minimally invasive procedure to provide access to the lock thereof so that it can be unlocked to allow the relative axial positioning between stabilization members 102, 104 to be adjusted.

In other procedures, the force of the biasing member 75 can be selected to allow lengthening of the stabilization members 102, 104 between anchors upon application of a threshold force that results due to spinal motion or growth of the patient's anatomy. The lock prevents or limits shortening of the length between the anchors, while the overall length of the stabilization members 102, 104 between anchors 106 increases over time by compression of the biasing member 75.

In other procedures, the surgeon can elect to apply distraction between the anchors 106 by increasing the length of the stabilization members 102, 104 between anchors 106 and then securing the stabilization members at this distraction length with coupling system 10, 110. The surgeon can also elect to apply compression between the anchors 106 by decreasing the length of the stabilization members 102, 104 between anchors 106 and then securing the stabilization members at this compression length with coupling system 10, 110. In still other procedures, the biasing member is selected to provide a biasing force that is maintained until a threshold tension force is exerted on the stabilization members 102, 104. This releases the locking force supplied by the biasing member to allow the length of the stabilization members 102, 104 to increase when the threshold force is exceeded. The biasing member automatically re-locks the stabilization members 102, 104 in the adjusted axial positioning relative to one another to maintain a minimum adjusted length of stabilization members 102, 104 between anchors 106.

It should be appreciated that stabilization members 102, 104 and the components of coupling system 10 contemplated herein may be composed of a single material or may be composed of a plurality of materials. For example, in one form the coupling member may be formed of one or more of medical grade stainless steel, titanium, chrome-cobalt, nitinol or other shape memory alloys, and one or more polymers. It is further contemplated that one or more portions of the coupling systems may be formed from a first material while another portion is formed from a different second material. For example, in one embodiment one or more of the components may be formed from a polymer while the rest of the components are formed of metallic material. In another form, one or more of the stabilization members may comprise one or more materials the same or different from each other. It should further be appreciated that the selection of material comprising the stabilization members may vary in relation to the selected flexibility and rigidity characteristics of the stabilization system.

In the embodiments illustrated herein, although only one coupling member is shown, one or more of the illustrated first and second stabilization members can be adapted for engagement with another coupling member at each end thereof so that three or more stabilization members may comprise the stabilization system. The stabilization members include stabilization member portions extending from the coupling member or members which are secured to vertebrae of the spinal column system with an anchor that may comprise any one or combination of hooks, screws, bolts, multi-axial screws, staples, cables or wires, sutures, clamps, and/or other attachment devices and systems, with or without interbody fusion devices or implants between vertebrae. Furthermore, the coupling systems 10, 110 can be oriented so that the first passage of first member 20, 20' is oriented to receive an end portion of stabilization member 104. Furthermore, the end portion of stabilization member 104 can be integral with the body portion of member 104 that is positionable along the spinal column, or the end portion can be removably attached to the body portion such as shown with second member 170 and stabilization member 102.

The coupling systems contemplated herein allow stabilization members of differing characteristics and stabilization members having the same characteristics to be adjustably secured relative to one another in end-to-end fashion to provide a stabilization system that is adapted for the anatomy, surgical condition, or surgical procedure. In one embodiment, the characteristic includes a cross-sectional dimension of the stabilization member portions so that stabilization members of differing sizes can be secured along the spinal column and to one another in end-to-end fashion. Other embodiments contemplate selection criteria for selection and assembly of the stabilization members to include any one or combination of characteristics, including length, contouring, flexibility, surface features, shape, section modulus, elasticity, materials and material properties, and coatings, for example. In still other embodiments, first and second stabilization members are provided with the same or substantially identical characteristics.

Engaging members 90 are positionable in the respective trans-axial bores 28, 168 and engageable to respective ones of the stabilization members 102, 104 to prevent the stabilization members from disengaging from coupling system 10. In one embodiment the stabilization members includes flats, recesses, receptacles or other configuration to receive or engage the engaging member 90 so that rotation of the stabilization member about its axis is resisted or prevented. In another embodiment, the stabilization members include threads or other structure on the ends thereof to positively engage the respective component of coupling system 10.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected.

What is claimed is:

1. A spinal stabilization system, comprising:
a first elongated stabilization member positionable along at least one vertebra and extending along a longitudinal axis between a first end and an opposite second end;
a second elongated stabilization member positionable along at least one other vertebra and extending along said longitudinal axis between a first end and an opposite second end, wherein said first end of said first stabilization member and said second end of said second stabilization member are positioned adjacent to one another;
a first bone anchor engageable to the at least one vertebra and engaged to the second end of the first stabilization member;
a second bone anchor engageable to the at least one other vertebra and engaged to the first end of the second stabilization member; and
a coupling system including a first member having a first end engaged to an end portion at said first end of said first stabilization member, wherein said first member includes a first wall section around said first passage adjacent said first end of said first member and a second wall section around said first passage that is spaced away from said first end of said first member, said first wall section defining a greater width than said second wall section and said first member further comprising a tapered wall section extending between said first wall section and said second wall section; and
a second end engaged to said second end of said second stabilization member, wherein said coupling system further includes a lock coupled between said first member and said end portion of said first stabilization member that has a locked position configured to maintain a relative axial positioning of said first and second stabilization members, wherein said lock includes a lock body extending about said end portion of said first stabilization member and a locking element configured to enter into at least one opening in said lock body when in a locked position wherein said lock body and said end portion are received in a first passage opening at said first end of said first member;
said lock further includes a biasing member biasing said lock body into said first passage to said locked position, and
said tapered wall section contacts said locking element and forces said locking element into said at least one opening in said lock body to contact said end portion of said first stabilization member in said first passage of said first member, and
said lock being movable along said longitudinal axis to release said end portion of said first stabilization member from said first member to allow the relative axial positioning of said first and second stabilization members to be adjusted.

2. The spinal of claim 1, wherein said end portion of said first stabilization member includes a second member to said first end of said first stabilization member and said second member is engaged to said first member with said lock.

3. The spinal stabilization system of claim 2, wherein said second member includes a first end portion having a receiving passage to receive said first end of said first stabilization member therein and at least one engaging member engageable to said first end portion to secure said first end of said first stabilization member in said receiving passage, said second member further including a second end portion extending from said first end portion, said second end portion being axially received in a first passage of said first member.

4. The spinal stabilization system of claim 3, wherein said lock includes a lock body in said first passage between said second end portion and said first member.

5. The spinal stabilization system of claim 4, wherein lock body includes an outer end extending outwardly from said first passage at a first end of said first member and said lock body includes an inner end in said first passage of said first member, said lock body further including at least one outer opening adjacent said outer end and further comprising a locking element in said at least one outer opening contacting said second end portion of said second member and said first end of said first member in said locked position.

6. The spinal stabilization system of claim 5, wherein said first end of said first member includes an inwardly tapered wall section contacting said locking element in said locked position.

7. The spinal stabilization system of claim 6, further comprising a biasing element engaged between said first member and said lock body biasing said lock body toward said locked position.

8. The spinal stabilization system of claim 6, wherein said second end portion of said second member includes a series of grooves extending thereabout and spaced axially along said second end portion for said locking element.

9. The spinal stabilization system of claim 3, wherein said first member includes a second passage opposite said first passage, and said second end of said second stabilization member is axially received in said second passage and further comprising an engaging member engageable with said first member to secure said second stabilization member in said second passage.

10. The spinal stabilization of claim 1, wherein said first end of said first stabilization member is axially received in a first passage extending into said first member from a first end of said first member and said second end of said second stabilization member is axially received in a second passage of said first member that opens at a second end of said first member opposite said first end of said first member.

11. The spinal stabilization system of claim 10, wherein said first member includes at least one trans-axial bore and further comprising at least one engaging member engaging said first member in said bore to secure said second stabilization member in said second passage.

12. The spinal stabilization system of claim 11, wherein said first member includes a solid partition wall between said first and second passages.

13. The spinal stabilization system of claim 11, wherein said first and second passages and said first and second stabilization members are in axial alignment along said longitudinal axis.

14. The spinal stabilization system of claim 1, wherein said lock body is movable against said biasing member to align said at least one opening and said locking element with said first wall section and allow said end portion to axially translate in said first passage to adjust relative axial positioning of said first and second stabilization members.

15. The spinal stabilization system of claim 1, wherein said at least one opening includes a plurality of openings about said lock body and said lock includes a locking element associated with each of said plurality of openings.

16. The spinal stabilization system of claim 1, wherein said first and second elongated spinal stabilization members each include a spinal rod portion extending along the respective vertebra.

17. The spinal stabilization system of claim 1, wherein said lock extends outwardly from said first end of said first member to a cap, said cap being connected to said lock and configured for grasping to displace said lock along said longitudinal toward said first elongated member to release said end portion from said locked position, wherein said first stabilization member extends along said longitudinal axis through and outwardly from said cap in a direction away from said second stabilization member.

18. The spinal stabilization of claim 1, wherein said first and second elongated stabilization members include a combined length from said second end of said first stabilization member to said first end of said second stabilization member sized to at least extend across a spinal disc space to vertebrae adjacent the spinal disc space.

19. A spinal stabilization system, comprising:
 a first elongated stabilization member positionable along at least one vertebra and extending along a longitudinal axis between a first end and an opposite second end;
 a second elongated stabilization member positionable along at least one other vertebra and extending along said longitudinal axis between a first end and an opposite second end, wherein said first end of said first stabilization member and said second end of said second stabilization member are positioned adjacent to one another, wherein said first and second elongated stabilization members include a combined length from said second of said first stabilization member to said first end of said second stabilization member sized to at least extend across a spinal disc space to vertebrae adjacent the spinal disc space; and
 a coupling system including a lock, a first member having a first end engaged to an end portion at said first end of said first stabilization member and a second end engaged to said second end of said second stabilization member, wherein said end portion of said first stabilization member is engaged in a passage of said first member by said lock being axially biased to a locked position to maintain a relative axial positioning of said first and second stabilization members,
 wherein said coupling system includes a lock body in said first passage between said end portion of said first stabilization member and said first member, said coupling member further including a biasing member engaged between said first member and said lock body to normally bias said lock body to said locked position, and
 said coupling system being operable to release said end portion from said locked portion to allow the relative axial positioning of said first and second stabilization members to be adjusted.

20. The spinal stabilization system of claim 19, wherein said coupling system includes at least one opening in said lock body and at least one locking element in said at least one opening, said at least one locking element engaging both of said end portion and said first member in said locked position.

21. The spinal stabilization system of claim 19, wherein said first member includes a second passage extending along said longitudinal axis and opening at a second end of said first member opposite said first end of said first member and said second end of said second stabilization member is received in said second passage.

22. The spinal stabilization system of claim 21, wherein said first member includes at least one bore extending transversely to said longitudinal axis and in communication with said second passage and further comprising an engaging member engaged to said first member in said at least one bore and engaging said second stabilization member in said second passage.

23. The spinal stabilization system of claim 19, wherein said first and second elongated spinal stabilization members each include a spinal rod portion extending along the respective vertebra.

24. The spinal stabilization system of claim 19, wherein said lock extends outwardly from said first end of said first member to a cap, said cap being connected to said lock and configured for grasping to displace said lock along said longitudinal toward said first elongated stabilization member and against said axial bias to release said end portion from said locked position, wherein said first stabilization member extends along said longitudinal axis through and outwardly from said cap in a direction away from said second stabilization member.

25. The spinal stabilization system of claim 19, further comprising:
 a first bone anchor engageable to the at least one vertebra and engaged to the second end of the first stabilization member; and
 a second bone anchor engageable to the at least one other vertebra and engaged to the first end of the second stabilization member.

* * * * *